United States Patent [19]

Otis

[11] Patent Number: 4,587,856
[45] Date of Patent: May 13, 1986

[54] NON-POLLUTING SAMPLER

[75] Inventor: Bradley A. Otis, Webster, Tex.

[73] Assignee: Shell Oil Company, Houston, Tex.

[21] Appl. No.: 768,186

[22] Filed: Aug. 23, 1985

Related U.S. Application Data

[63] Continuation of Ser. No. 597,763, Apr. 6, 1984, abandoned.

[51] Int. Cl.$^4$ ............................................. G01N 1/20
[52] U.S. Cl. ............................... 73/863.51; 73/863.81
[58] Field of Search ............ 73/863.32, 863.44, 863.51, 73/863.52, 863.53, 863.54, 863.81, 863.83, 863.85, 863.86; 251/326

[56] References Cited

U.S. PATENT DOCUMENTS

| | | | |
|---|---|---|---|
| 608,834 | 8/1898 | Byrnes | 73/863.51 X |
| 1,649,241 | 11/1927 | Lewis | 73/863.51 |
| 1,966,712 | 7/1934 | Fisher et al. | 73/863.54 |
| 2,683,373 | 7/1954 | Gallup et al. | 73/863.53 |
| 2,815,664 | 12/1957 | Dawes et al. | 73/863.81 |
| 3,066,539 | 12/1962 | Coker et al. | 73/863.54 |
| 3,076,341 | 2/1963 | Murray et al. | 73/863.53 |
| 3,260,120 | 7/1966 | Stilwell | 73/863.54 |
| 3,276,264 | 10/1966 | Banks | 73/863.54 |
| 3,381,537 | 5/1968 | Goodson et al. | 73/863.51 |
| 3,659,461 | 5/1972 | Thompson | 73/863.83 X |
| 3,713,342 | 1/1973 | Jirik | 73/863.53 |
| 3,754,443 | 8/1973 | Harris, Sr. et al. | 73/863.81 |
| 3,858,449 | 1/1975 | Singer | 73/863.83 |
| 3,859,857 | 1/1975 | Falk | 73/863.51 |
| 4,009,727 | 3/1977 | Bailey | 251/326 X |
| 4,433,587 | 2/1984 | Risdal | 73/863.83 X |
| 4,481,833 | 11/1984 | Bajek | 73/863.81 X |

Primary Examiner—Richard L. Chiesa

[57] ABSTRACT

Solids are sampled without releasing dust and fumes by bolting to a solids chute a sampling arrangement including a knife gate valve, a sampler housing and a sliding sampler canister that maintains a seal along the housing wall when the valve is open.

4 Claims, 1 Drawing Figure

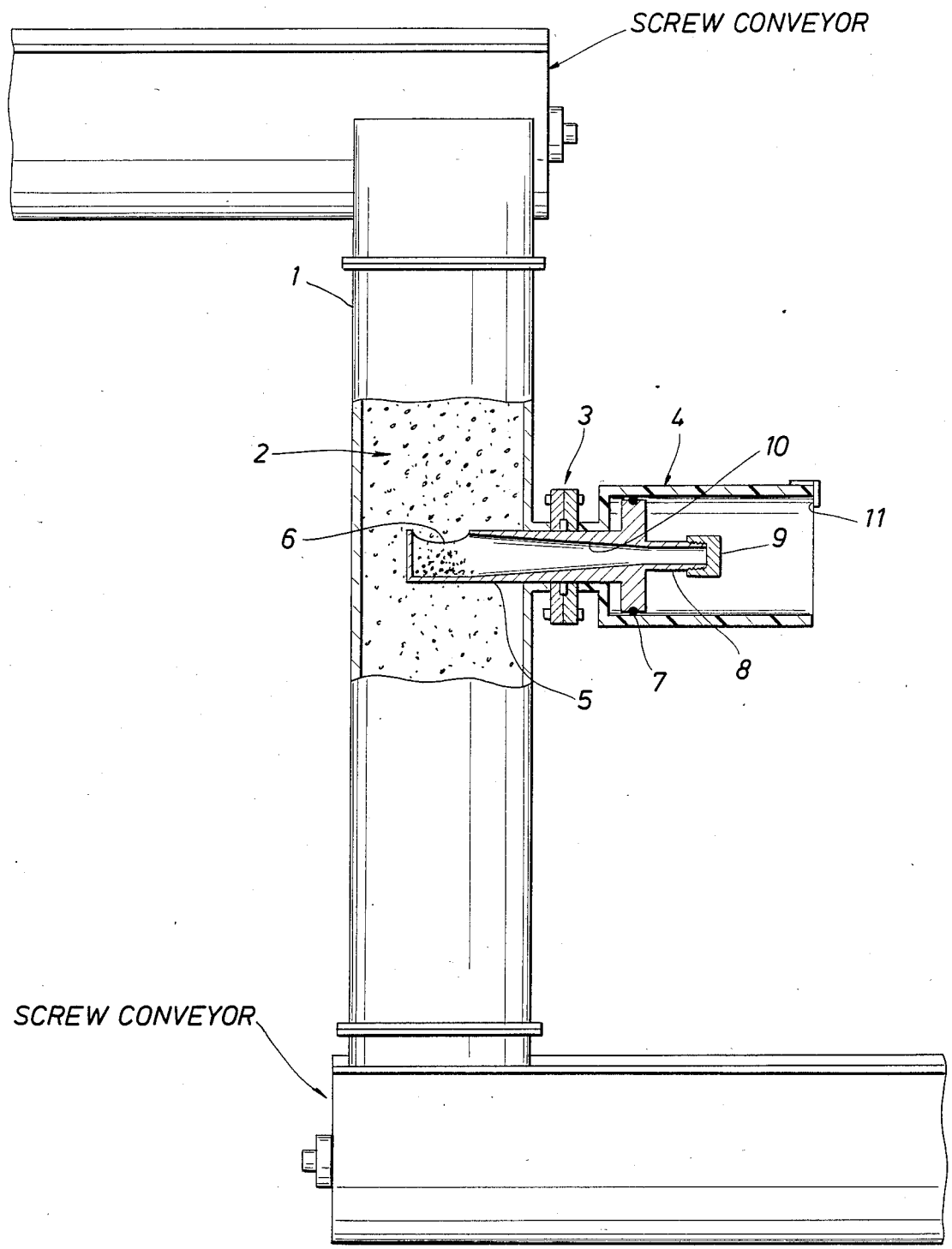

NON-POLLUTING SAMPLER

This is a continuation of application Ser. No. 597,763, filed Apr. 6, 1984, now abandoned.

BACKGROUND OF THE INVENTION

The present invention relates to an apparatus for sampling material moving through a pipe or chute in a generally vertically downward direction. More particularly, the invention relates to such a sampler capable of obtaining samples from a chute which may be pressurized without releasing significant portions of dust or fumes into the atmosphere.

Various previously known sampling devices are described in U.S. patents such as the following: U.S. Pat. No. 608,834 describes a sampling machine that discharges samples through the atmosphere into a receiver. U.S. Pat. No. 1,649,241 describes a sampler designed for unattended automatic operation while sampling milk or other liquid. U.S. Pat. No. 1,966,712 describes an automatic sampler for periodically being air driven into a collecting position and spring returned into a sample discharging position. U.S. Pat. No. 2,683,373 describes a grain sampling cup arranged to be reciprocated and rotated from a chute closing position to a sample collecting position along a vertical grain chute. U.S. Pat. No. 3,076,341 describes a sampling cup which is automatically rotated from a non-collecting to a collecting position as it is moved into a product chute. U.S. Pat. No. 3,381,537 describes an inclined tubular sampler arranged for continuously discharging particles, which are collected by selectively shaped openings, through the atmosphere into a sample receiving hopper.

SUMMARY OF THE INVENTION

The present invention relates to sampling particles or liquids moving generally downwardly through a chute without allowing significant amounts of gas or dust to be discharged into or out of the chute or the surrounding atmosphere. A full opening valve is connected between the interior of the chute and an open ended tube. A tubular canister is arranged to have a sampling chamber, near its front, and a seal capable of slidably engaging and sealing against the inner surface of the open ended tube, near the rear of the canister. The canister dimensions are arranged so that the seal can engage the wall of the open ended tube when the canister is inserted within the open ended tube while the valve is closed, the sampling chamber can move through the valve and into the chute when the valve is open, and the seal remains engaged with the tube wall when the sampling chamber is inserted into the chute. Means are provided for operating the valve and inserting the chamber.

BRIEF DESCRIPTION OF THE DRAWING

The sole drawing FIGURE is a schematic illustration of a particle conveying chute to which the sampling device of the present invention is attached.

DESCRIPTION OF THE INVENTION

The sole drawing FIGURE shows a chute 1 through which particles 2 are moving in a downward direction. The present invention is applicable to such a chute or pipe through which substantially any particles and/or liquids are flowed in a generally downward direction by gravity and/or a pressure gradient. Such particles can be pneumatically conveyed or blanketed by a gas such as nitrogen or the like under pressure greater than atmospheric pressure or sucked toward a zone of reduced pressure. However, as will be apparent to those skilled in the art, if the chute pressures are more than a few pounds per square inch above or below atmospheric pressure, it may be desirable to use samplers having relatively small cross sectional areas and/or mechanical aids for moving the sample-collecting chamber into or out of the chute.

A substantially full opening valve 3 is connected to the chute to open a passageway between the interior of the chute and the interior of an open ended tube 4 which is connected to the valve. In a preferred embodiment for use with solid particles the valve 3 is a knife gate valve and the tubing 4 is constructed of a plastic material having a relatively low coefficient of friction, such as Teflon, to facilitate the insertion and withdrawal of the canister.

A sampling canister 5 is provided with a sample collecting chamber 6 near its front and a seal 7 for slidably engaging the inner wall of the tube 4 near its rear. A handle 8 with a screw cap 9 is attached to the canister 5 to facilitate its movement and handling. The canister dimensions are such that the canister front is short of the valve closure when the seal 7 has engaged the inner wall of tube 4, and the seal remains engaged with the wall when the canister is advanced to position the sampling chamber 6 within the chute 1.

The canister handle is preferably hollow and provided with an inner wall surface 8 shaped generally as a funnel so that a sample can flow from the sample collecting chamber through the handle when the cap 9 is removed.

A canister travel stopping latch 11 is preferably arranged on the outer end of the tubing 4 to prevent an accidental withdrawing of the canister to a position unseating the seal 7 before the valve 3 is closed.

In a preferred operating procedure, while the valve 3 is closed, the canister 5 is inserted far enough to engage the seal 7 with the interior wall of the tubing 4. The valve 3 is then opened and the canister advanced into the chute 1 to collect a sample. The canister is then retracted to the stopping latch so that it clears the valve 3 and the valve is closed. The canister is then removed. After removing the cap 9, the collected sample can be poured through the hollow handle of the canister into a sample collecting bag or other container, so that substantially no fluid or dust is allowed to flow into or out of the chute or the atmosphere.

What is claimed is:
1. Apparatus for sampling pneumatically and/or gravitationally conveyed particulate said material moving generally downward through a chute without allowing significant portions of gas or dust to be displaced into or out of the chute, comprising:
   a substantially full opening knife gate valve connected between an opening in the wall of the chute and an opening into an open ended tube, with that valve arranged for confining gas and dust within the chute when the valve is closed and the open ended tube is empty;
   a readily detachable tubular canister arranged to have a sample receiving chamber in which there is an open inlet but not an open outlet for receiving and retaining solid particles amounting to a sample having a size limited to a selected magnitude near its front and a seal capable of slidably engaging the interior of the open ended tube near its rear, said canister having dimensions arranged so that the seal can engage the tube wall when the canister is within the tube with the valve closed, the canister sample receiving chamber can be advanced through the valve and into the chute when the valve is open, and the seal can remain in engagement with the tubing wall during the advancing of the sample receiving chamber into the interior of the chute; and means for operating the valve and moving the canister.

2. The apparatus of claim 1 in which the canister is provided with a hollow handle through which a collected sample can be transferred to a sample container.

3. The apparatus of claim 1 in which the open ended tubing is provided with a stop latch to prevent a retraction of the canister to a point releasing the seal between it and the tubing wall before the valve is closed.

4. The apparatus of claim 1 in which the tubing and canister are constructed of plastic material having a relatively low coefficient of friction.

* * * * *